United States Patent [19]

Fisher et al.

[11] Patent Number: 5,693,590

[45] Date of Patent: Dec. 2, 1997

[54] COMPOSITIONS CONTAINING PHOSPHOSULFONATE HERBICIDES AND DICHLOROACETAMIDE SAFENERS

[75] Inventors: James Delbert Fisher, Lansdale; Ernest Leroy Burdge, Pennsburg; Vincent Angelo Musco, Jr., Southampton; Lori Ann Spangler, Churchville, all of Pa.

[73] Assignee: Rohm and Haas Company, Philadelphia, Pa.

[21] Appl. No.: 504,621

[22] Filed: Jul. 20, 1995

Related U.S. Application Data

[63] Continuation of Ser. No. 298,529, Aug. 30, 1994, abandoned.

[51] Int. Cl.$^6$ ............................................ A01N 31/04
[52] U.S. Cl. ................ 504/105; 504/106; 504/107; 504/108; 504/112; 504/194; 504/195; 504/196; 504/197; 504/199; 504/200; 504/201; 504/207; 504/208
[58] Field of Search .................... 504/194, 195, 504/196, 197, 199, 200, 201, 207, 208, 105, 106, 108, 112, 107

[56] References Cited

U.S. PATENT DOCUMENTS 4,137,070  1/1979  Pallos et al. .
5,272,128  12/1993  Rosen et al. .

FOREIGN PATENT DOCUMENTS 304409  2/1989  European Pat. Off. .
524394  4/1993  European Pat. Off. .

*Primary Examiner*—Brian M. Burn
*Attorney, Agent, or Firm*—Clark R. Carpenter

[57] ABSTRACT

This invention pertains to compositions comprising herbicidal phosphosulfonates, having the general formula

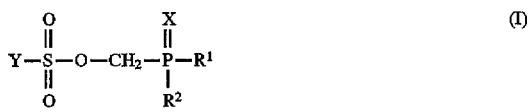

wherein Y is an optionally substituted phenyl, naphthyl, benzyl, a $(C_5-C_8)$cycloalkyl, a 5-membered heteroaromatic ring, a 6-membered heteraromatic ring, a fused 5,6-membered heteroaromatic ring, or a fused 6,6-membered heteroaromatic ring;

X is an oxygen or a sulfur atom; and $R^1$ and $R^2$ are each independently selected from substituted or unsubstituted alkyl, alkoxy, alkylthio, alkenyloxy, alkynyloxy, haloalkoxy, cyanoalkoxy, alkoxyalkoxy, cycloalkyloxy, cycloalkylalkoxy, alkylideneiminooxy, chloro, amino, phenyl or phenoxy; or $R^1$ and $R^2$ are both alkoxy, taken together with the phosphorus atom to form a 6-membered oxygen-containing ring; and dichloroacetamide safeners having the general formula

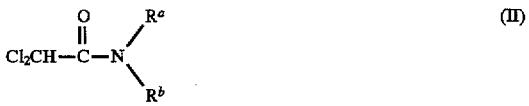

wherein $R^a$ and $R^b$ are each independently selected from alkyl, alkenyl, or alkyl or alkenyl substituted with halo, or $R^a$ and $R^b$ together with the nitrogen atom to which they are attached form a 5- or 6-membered substituted heterocyclic ring;

and the use of these compositions as selective herbicides.

15 Claims, No Drawings

COMPOSITIONS CONTAINING PHOSPHOSULFONATE HERBICIDES AND DICHLOROACETAMIDE SAFENERS

This application is a continuation of Ser. No. 08/298,529, filed Aug. 30, 1994, (now abandoned).

FIELD OF THE INVENTION

This invention pertains to herbicidal compositions comprising herbicidal phosphosulfonates and safeners such as dichloroacetamides and the use of these compositions as herbicides.

BACKGROUND OF THE INVENTION

Typical compositions containing chemical weed control agents enable more efficient crop production by minimization of competing plant growth. New chemical means of controlling such unwanted vegetation are desirable to obtain better control of various agronomically important weeds, for better crop safety and to overcome herbicide resistance.

The herbicidal compounds of the compositions of this invention provide control of many weed species, particularly grassy weeds. Although they may be used before or after the plant has emerged from the soil, they are especially effective when used to control growth of unwanted plants before the plants emerge from the soil.

The herbicidal phosphosulfonate compounds of these compositions primarily interfere with critical life processes in the germinating seed or seedling either causing plant death before growth above the soil or severely retarding growth of the plant so that the weed seedling does not compete with the growing crop. However, a common problem with highly active herbicidal compounds is one of selectivity to certain crops. Selectivity refers to the ability of a herbicide to retard the growth of or kill weed species without damaging crop plants. Retardation of weed growth may only be necessary for a time sufficiently long for the desired crop to become dominant. Effective control of weeds, especially monocot weeds such as Green Foxtail (*Setaria viridis*), Barnyardgrass (*Echinochloa crus-galli*), Blackgrass (*Alopecurus myosuroides*), Canarygrass (*Phalaris minor*), Bermudagrass (*Cynodon dactylon*), Johnsongrass (*Sorghum halepense*), Ryegrass (*Lolium multiflorum*), Signalgrass (*Brachiaria platyphylla*), Sprangletop (*Leptochloa dubia*) and Crabgrass (*Digitaria sanguinalis*), and dicot weeds such as Velvetleaf (*Abutilon theophrasti*), Beggarweed (*Desmodium tortuosom*), Hairy Beggarticks (*Bidens pilosa*), Curly Dock (*Rumex crispus*), Pineappleweed (*Matricaria matricarioides*), Pigweed (*Amaranthus retroflexus*), Teaweed (*Sida spinosa*) and Speedwell (*Veronica officinalis*) can be difficult to accomplish without injury to the desired crop, especially a monocot crop such as corn (*Zea mays*), sorghum (Sorghum spp.), rice (*Oryza sativa*), wheat (Triticum spp.), barley (*Hardeum sativum*) and the like and dicot crops such as soybean (*Glycine max*), cotton (Gossypium spp.) and the like.

It has been found that the herbicidal compositions of this invention comprising one or more phosphosulfonate herbicides, a dichloroacetamide safener and an agronomically acceptable carrier avoid this problem of providing effective weed control while simultaneously providing complete safety to the desired crop. The herbicidal compositions may be applied to the desired crop or to the locus where the desired crop is to be grown either after the emergence of the undesired weed vegetation or, preferably, before the emergence of the undesired weed vegetation. Thus, the compositions of this invention control the growth of weeds while generally not injuring crops. The herbicidal compositions of this invention also may be applied to the desired crop seed as an alternate treatment utility whereby the safener is first applied to the seed followed by preemergence application of the herbicide.

SUMMARY OF THE INVENTION

The herbicidal compositions of this invention comprise (i) one or more phosphosulfonate herbicides having the general formula

wherein (1) Y is selected from phenyl; naphthyl; benzyl; ($C_5$–$C_8$) cycloalkyl; a 5-membered heteroaromatic ring having 1, 2, 3, or 4 heteroatoms independently selected from the group consisting of nitrogen, oxygen and sulfur atoms provided no more than one heteroatom is oxygen or sulfur; a 6-membered heteroaromatic ring having 1, 2 or 3 nitrogen atoms; a fused 5,6-membered heteroaromatic ring having 1–4 heteroatoms independently selected from the group consisting of nitrogen, oxygen and sulfur atoms provided no more than one heteroatom is oxygen or sulfur; or a fused 6,6-membered heteroaromatic ring having 1–4 heteroatoms independently selected from the group consisting of nitrogen, oxygen and sulfur atoms provided no more than one heteroatom is oxygen or sulfur;

wherein each of said Y may be substituted with up to three substituents each independently selected from halo, cyano, nitro, alkoxy, haloalkoxy, alkyl, haloalkyl, phenyl, alkylcarbonyloxy, dialkylcarbamoyl, alkylthio, haloalkylthio, arylthio, aryloxy, formyl, alkylcarbonyl, arylcarbonyl, dialkylamino, methoxymethyl, methylthiomethyl and alkoxycarbonyl, provided (a) there is at most one of said substituents on said Y when Y is a thiadiazolyl ring or a tetrazolyl ring, (b) there is at most two of said substituents when Y is a triazolyl ring, a thiazolyl ring, or an isothiazolyl ring, and (c) when Y is phenyl, naphthyl or benzyl, there can be one to five of said previously described substituents;

(2) X is an oxygen or a sulfur atom; and (3) $R^1$ and $R^2$ are each independently selected from alkyl, alkoxy, alkylthio, alkenyloxy, alkynyloxy, haloalkoxy, cyanoalkoxy, alkoxyalkoxy, cycloalkyloxy, cycloalkylalkoxy, alkylideneiminooxy, chloro and amino with one or two substituents selected from the group consisting of alkyl, alkenyl and phenyl; provided that there is no more than one phenyl group on the amino group, and provided that $R^1$ may be selected additionally from phenyl or phenoxy; and provided that $R^1$ and $R^2$ both can be alkoxy, taken together with the phosphorus atom to form a 6-membered oxygen-containing ring, except that when $R^1$ and $R^2$ are both alkoxy, Y is not phenyl, 4-methylphenyl, 4-chlorophenyl, 4-bromophenyl or 3-nitrophenyl;

(ii) a dichloroacetamide safener having the general formula

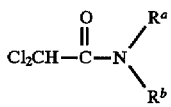 (II)

wherein $R^a$ and $R^b$ are each independently selected from alkyl, alkenyl, or alkyl or alkenyl substituted with halo, or $R^a$ and $R^b$ together with the nitrogen atom to which they are attached form a 5- or 6-membered substituted heterocyclic ring selected from the group consisting of

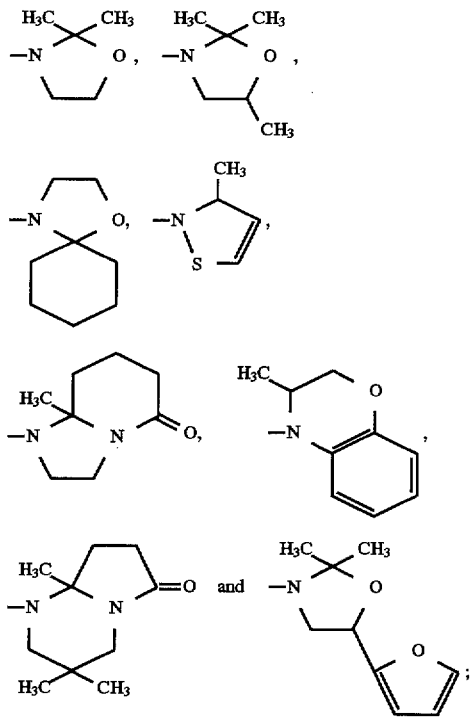

and an agronomically acceptable carrier.

DETAILED DESCRIPTION OF THE INVENTION

As used to describe the present invention, the term "alkyl", whether alone or as part of another group, refers to a straight or branched chain alkyl. Examples of alkyl include (without limiting) methyl, ethyl, n-propyl, isopropyl, n-butyl, sec-butyl, isobutyl, tert-butyl, n-pentyl, isopentyl, neopentyl, hexyl, isohexyl, sec-hexyl, 2,2-dimethylbutyl and 2,3-dimethylbutyl; and, as further illustration, examples of alkoxy include methoxy, ethoxy, n-propoxy, isopropoxy, n-butoxy, sec-butoxy, isobutoxy, tert-butoxy, isopentoxy, n-pentoxy, neopentoxy, hexyloxy, isohexyloxy, sec-hexyloxy, 2,2-dimethylbutoxy and 2,3-dimethylbutoxy. "Haloalkyl" and "haloalkoxy" refer to an alkyl and alkoxy group, respectively, substituted with from one to five halogen atoms, preferably from one to three halogen atoms, preferably fluorine or chlorine atoms. Examples of haloalkyl and haloalkoxy include (without limiting) trifluoromethyl, difluoromethoxy, 2,2,2-trifluoroethoxy, 2-chloroethoxy, difluoromethyl, 2,2,2-trifluoroethyl, 3,3,3-trifluoropropyl, pentafluoroethyl and trifluoromethoxy. "Halo" includes fluoro, chloro, bromo and iodo. "Alkylthio" refers to an alkyl group attached to a sulfur atom. Examples include methylthio, ethylthio, n-propylthio, isopropylthio, n-butylthio, sec-butylthio, isobutylthio, t-butylthio. "Haloalkylthio" refers to an alkylthiogroup substituted with from one to five halogen atoms, preferably fluorine or chlorine atoms. Examples include trifluoromethylthio, difluoromethylthio, 2,2,2-trifluoroethylthio, 2-chloroethylthio, and pentafluoroethylthio. "Arylthio" and "aryloxy" mean an aromatic ring attached to a sulfur or oxygen respectively. Examples include phenylthio and phenyloxy. "Alkylcarbonyl" refers to a carbonyl group attached to an alkyl radical. Examples include methylcarbonyl, ethylcarbonyl, n-propylcarbonyl and isopropylcarbonyl. "Dialkylamino" refers to a nitrogen atom with two alkyl substituents, which may be the same or different. Examples include dimethylamino, diethylamino and methylethylamino. "Alkenyl" and "alkynyl", whether alone or as part of another group, refer to straight and branched chain alkenyl and alkynyl, respectively. Examples of alkenyl and alkynyl include (without limiting) allyl, propargyl and 1-methylpropargyl; and, as further illustration, examples of alkenyloxy and alkynyloxy include (without limiting) allyloxy, propargyloxy and 1-methylpropargyloxy. "Alkylideneiminooxy" refers to an alkyl group double bonded to nitrogen which is in turn bonded to oxygen. An example of alkylideneiminooxy is isopropylideneiminooxy. "Cycloalkyl", whether alone or as part of another group, refers to a monocyclic non-aromatic carbocyclic ring. Examples of cycloalkyl include (without limiting) cyclobutyl, cyclopentyl and cyclohexyl. Examples of heteroaromatic rings include (without limiting) thienyl, isoxazolyl, pyrazolyl, triazolyl, quinolinyl, imidazolopyridinyl, pyrimidinyl, benzothiadiazolyl, thiazolyl, pyridyl (alternatively termed "pyridinyl" and includes, but is not limited to, pyridinyl oxides) and thiadiazolyl.

In one embodiment of this invention are compositions comprising one or more herbicidal compounds of formula (I) and a safener compound of formula (II) and the use of those compositions to control weeds wherein Y is selected from phenyl, naphthyl, benzyl, a ($C_5$–$C_8$)cycloalkyl, a 5-membered heteroaromatic ring having 1, 2, 3 or 4 heteroatoms independently selected from the group consisting of nitrogen, oxygen and sulfur atoms provided no more than one heteroatom is oxygen or sulfur, a 6-membered heteroaromatic ring having 1, 2 or 3 nitrogen atoms, a fused 5,6-membered or fused 6,6-membered heteroaromatic ring having 1–4 heteroatoms independently selected from the group consisting of nitrogen, oxygen and sulfur atoms provided no more than one heteroatom is oxygen or sulfur; wherein each Y group may be substituted with up to three substituents each independently selected from halo, cyano, nitro, ($C_1$–$C_6$)alkoxy, halo($C_1$–$C_4$)alkoxy, ($C_1$–$C_6$)alkyl, halo($C_1$–$C_4$)alkyl, phenyl, ($C_1$–$C_4$)alkylcarbonyloxy, di($C_1$–$C_4$)alkylcarbamoyl, ($C_1$–$C_6$)alkylthio, halo($C_1$–$C_4$)alkylthio, arylthio, aryloxy, formyl, ($C_1$–$C_4$)alkylcarbonyl, arylcarbonyl, di($C_1$–$C_4$)alkylamino, methoxymethyl, methylthiomethyl and ($C_1$–$C_4$)alkoxycarbonyl, provided there is only one substituent on thiadiazolyl or tetrazolyl and further provided that triazolyl, thiazolyl or isothiazolyl can only have up to two substituents, or, wherein Y is phenyl, naphthyl or benzyl, each Y group may be substituted with one to five substituents selected from halo, acetoxy, methyl, methoxy, difluoromethoxy, trifluoromethoxy, ethyl, ethoxy, trifluoromethyl, pentafluoroethyl, methylthio, ethylthio, propylthio, trifluoromethylthio, methoxymethyl and methylthiomethyl; and provided that when $R^1$ and $R^2$ are both alkoxy, Y is not phenyl, 4-methylphenyl, 4-chlorophenyl, 4-bromophenyl or 3-nitrophenyl;

X is an oxygen or a sulfur atom, preferably an oxygen atom; and $R^1$ and $R^2$ are each independently selected from $(C_1-C_6)$ alkyl, $(C_1-C_6)$alkoxy, halo$(C_1-C_4)$alkoxy, $(C_1-C_4)$ alkylthio, $(C_3-C_4)$alkenyloxy, $(C_3-C_4)$alkynyloxy, $(C_1-C_4)$ alkoxy$(C_1-C_4)$alkoxy, $(C_4-C_8)$cycloalkyloxy, $(C_3-C_6)$ cycloalkyl$(C_1-C_3)$alkoxy, cyano$(C_1-C_4)$alkoxy, $(C_2-C_4)$ alkylideneiminooxy, chloro, and amino substituted with one or two substituents selected from $(C_1-C_4)$alkyl, $(C_2-C_4)$ alkenyl and phenyl provided there is not more than one phenyl group on the amino group, additionally, $R^1$ may be selected from phenyl or phenoxy; or $R^1$ and $R^2$ are both alkoxy, taken together with the phosphorous atom to form a 6-membered oxygen-containing ring;

$R^a$ and $R^b$ are each independently selected from $(C_2-C_4)$ alkyl, $(C_3-C_4)$alkenyl, $(C_2-C_4)$alkyl or $(C_3-C_4)$alkenyl substituted with halo, or $R^a$ and $R^b$ together with the nitrogen atom to which they are attached form the 5-membered heterocyclic moiety

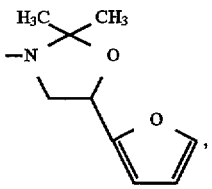

which together with the $Cl_2CH(O)$ moiety forms the compound 3-(dichloroacetyl)-5-(2-furyl)-2,2-dimethyl-1,3-oxazolidine which is also known as furilazole.

Preferred 5-membered heteroaromatic Y substitutents are thienyl, pyrazolyl, isoxazolyl, triazolyl, tetrazolyl, thiazolyl, isothiazolyl, pyrrolyl, thiadiazolyl, and imidazolyl. Preferred thienyls are 2-thienyl and 3-thienyl. Preferred pyrazolyls are pyrazol-3-yl, pyrazol-4-yl, and pyrazol-5-yl; more preferably 5-chloro-1-methyl-3-$(C_1-C_3)$alkyl-4-pyrazolyls, 5-chloro-1-methyl-3-alkyl-4-pyrazolyls and 1,5-di$(C_1-C_3)$ alkyl-3-trifluoromethyl-4-pyrazolyl wherein $R^1$ is isopropoxy; and $R^2$ is methyl, ethyl, methoxy, or ethoxy. Preferred triazolyls are 1,2,4-triazol-3-yl and 1,2,4-triazol-5-yl, which triazolyls optionally have a dimethylcarbamoyl substituent attached to a nitrogen atom. Preferred tetrazolyls are tetrazol-1-yl and tetrazol-5-yl. Preferred isoxazolyls are isoxazol-4-yl and isoxazol-5-yl. Preferred thiazolyls are thiazol-2-yl, thiazol-4-yl, and thiazol-5-yl. Preferred isothiazolyls are isothiazol-4-yl and isothiazol-5-yl. Preferred pyrrolyls are pyrrol-2-yl and pyrrol-3-yl. A preferred thiadiazolyl is 1,3,4-thiadiazol-2-yl. Preferred imidazolyls are imidazol-2-yl, imidazol-4-yl, and imidazol-5-yl.

Preferred 6-membered heteroaromatic Y substituents are pyridinyl, pyrazinyl, pyridazinyl, and pyrimidinyl. Preferred pyridinyls are pyridin-2-yl and pyridin-3-yl. Other preferred pyridinyls are pyridin-2-yl N-oxide and pyridin-3-yl N-oxide. A preferred pyrazinyl is pyrazin-2-yl. A preferred pyridazinyl is pyridazin-3-yl. Preferred pyrimidinyls are pyrimidin-2-yl, pyrimidin-4-yl, and pyrimidin-5-yl.

Preferred fused 5,6-membered heteroaromatic Y substituents are indolyl, imidazolopyridinyl, pyrazolopyrimidinyl, benzoimidazolyl, benzothienyl, benzothiazolyl, thiadiazolyl, benzotriazolyl, and benzoxazolyl. Preferred indolyls are 1H-indol-2-yl and 1H-indol-3-yl. A preferred imidazolpyridinyl is imidazol[1,2-a]-pyridin-3-yl. A preferred pyrazolopyrimidinyl is pyrazolo[1,5-a]pyrimidin-3-yl. Preferred benzoimidazolyls are benzoimidazol-2-yl and benzoimidazol-7-yl. Preferred benzothienyls are benzo[b]thien-2-yl and benzo[b]thien-3-yl. Preferred benzothiazolyls are benzothiazol-2-yl and benzothiazol-7-yl. A preferred benzothiadiazolyl is benzo-2,1,3-thiadiazol-4-yl. A preferred benzotriazolyl is 2H-benzotriazol-4-yl. Preferred benzoxazolyls are benzoxazol-2-yl and benzoxazol-4-yl.

A preferred fused 6,6-membered heteroaromatic Y substituent is quinolinyl.

All of the above preferred 5-membered heteroaromatic Y substituents, preferred 6-membered heteroaromatic Y substituents, preferred fused 5,6-membered heteroaromatic Y substituents, and preferred fused 6,6-membered heteroaromatic Y substituents can be unsubstituted or can be substituted with up to three substituents each independently selected from halo, cyano, nitro, $(C_1-C_6)$alkoxy, halo$(C_1-C_4)$alkoxy, $(C_1-C_6)$alkyl, halo$(C_1-C_4)$alkyl, phenyl, $(C_1-C_4)$alkylcarbonyloxy, di$(C_1-C_4)$alkylcarbamoyl, $(C_1-C_6)$alkylthio, halo$(C_1-C_4)$alkylthio, arylthio, aryloxy, formyl, $(C_1-C_4)$alkylcarbonyl, arylcarbonyl, di$(C_1-C_4)$ alkylamino and $(C_1-C_4)$alkoxycarbonyl as specified hereinabove for all Y substituents.

In a preferred embodiment of this invention are compositions comprising one or more herbicidal compounds of formula (I) and a safener compound of formula (II) and the use of those compositions to control weeds wherein Y is (a) substituted phenyl, 1,2,4-triazol-3-yl, 1,2,4-triazol-5-yl, thien-2-yl (2-thienyl), thien-3-yl (3-thienyl), pyridin-2-yl (2-pyridinyl), pyridin-3-yl (3-pyridinyl), pyrimidin-2-yl (2-pyrimidinyl), pyrimidin-4-yl (4-pyrimidinyl), pyrimidin-5-yl (5-pyrimidinyl), pyrazol-4-yl (4-pyrazolyl), pyrazol-5-yl (5-pyrazolyl), isoxazol-4-yl (4-isoxazolyl), benzo-2,1,3-thiadiazol-4-yl (4-benzo-2,1,3-thiadiazolyl), thiazol-5-yl (5-thiazolyl), and quinolin-8-yl (8-quinolinyl), each Y group having up to three substituents selected from halo, cyano, $(C_1-C_4)$alkyl, $(C_1-C_4)$alkoxy, halo$(C_1-C_4)$alkoxy, halo $(C_1-C_4)$alkyl, $(C_1-C_2)$alkylcarbonyloxy, di$(C_1-C_3)$ alkylcarbamoyl, and $(C_1-C_3)$alkoxycarbonyl; or (b) substituted phenyl having four or five substituents selected from fluoro, chloro, bromo, methyl, methoxy, difluoromethoxy, trifluoromethoxy, ethyl, ethoxy, n-propoxy, trifluoromethyl, pentafluoroethyl, methylthio, ethylthio, trifluoromethylthio and acetoxy;

X is an oxygen atom;

$R^1$ and $R^2$ are each independently $(C_1-C_4)$alkyl, $(C_1-C_4)$ alkoxy, $(C_1-C_2)$alkoxy$(C_1-C_2)$alkoxy, halo$(C_1-C_4)$alkoxy, $(C_3-C_4)$alkenyloxy, $(C_3-C_4)$alkynyloxy, cyano$(C_1-C_4)$ alkoxy and $(C_4-C_6)$cycloalkoxy; provided $R^1$ and $R^2$ are not both alkyl and that when $R^1$ and $R^2$ are both alkoxy, Y is not phenyl, 4-methylphenyl, 4-chlorophenyl, 4-bromophenyl or 3-nitrophenyl; and $R^a$ and $R^b$ are each independently selected from ethyl, n-propyl, allyl, or ethyl, n-propyl or allyl substituted with chloro, or $R^a$ and $R^b$ together with the nitrogen atom to which they are attached form the 5-membered heterocyclic moiety

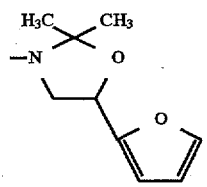

A more preferred embodiment of this invention is where Y is phenyl having up to three substituents, one of which is at the ortho position, independently selected from halo, halo$(C_1-C_2)$alkyl, $(C_1-C_2)$alkoxy, halo$(C_1-C_2)$alkoxy and $(C_1-C_4)$alkyl provided when there are three substituents no more than two substituents are concurrently alkoxy or alkyl; X is an oxygen atom; and $R^1$ and $R^2$ are each independently selected from $(C_1-C_2)$alkyl and $(C_1-C_3)$alkoxy, provided $R^1$ and $R^2$ are not both alkyl; and $R^a$ and $R^b$ are each independently allyl, 3,3-dichloroallyl, or $R^a$ and $R^b$ together with the nitrogen atom to which they are attached form the 5-membered heterocyclic moiety

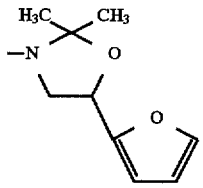

In an even more preferred embodiment of this invention Y is phenyl, monosubstituted in its ortho position, the substituent being independently selected from chloro, bromo, trifluoromethoxy, trifluoromethylthio, methylthio, ethylthio and trifluoromethyl; X is an oxygen atom; $R^1$ is selected from methoxy, ethoxy, isopropoxy, methyl and ethyl and $R^2$ is selected from ethoxy and isopropoxy; and $R^a$ and $R^b$ are each allyl which together with the $Cl_2CH(O)$ moiety forms the compound N,N-diallyl-2,2-dichloroacetamide which is also known as dichlormid, or $R^a$ and $R^b$ together with the nitrogen atom to which they are attached form the 5-membered heterocyclic moiety

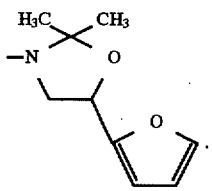

Additionally, Y may have a second substituent in its second ortho position selected from chloro, bromo, methyl, ethyl, isopropyl, methoxy, trifluoromethyl, difluoromethyl, difluoromethoxy, trifluoromethylthio, methylthio, ethylthio, pentafluoroethyl, fluoro, ethoxy and trifluoromethoxy. Further, Y may be trisubstituted with fluoro, chloro or bromo at the two ortho positions and methyl or ethyl at the meta position.

Most preferably, Y is 2-chlorophenyl, 2-bromophenyl, 2,6-dichlorophenyl, 2-trifluoromethylphenyl, 2-chloro-6-isopropylphenyl, 2-chloro-6-methylphenyl, 2-methyl-6-trifluoromethylphenyl, 2-methoxy-6-trifluoromethylphenyl, 2-trifluoromethoxyphenyl, 2-methylthiophenyl, 2-ethylthiophenyl, 2-trifluoromethylthiophenyl, 2-trifluoromethy-6-fluorophenyl, 2-trifluoromethyl-6-ethylphenyl, 2-trifluoromethyl-4-fluorophenyl, 2-trifluoromethyl-6-ethoxyphenyl, 2,5-difluorophenyl, 2-trifluoromethoxy-6-fluorophenyl, 2-trifluoromethyl-6-methylthiophenyl, 2-trifluoromethyl-6-ethylthiophenyl, 2-trifluoromethylthio-4-fluorophenyl, 2-trifluoromethylthio-6-methylphenyl, 2-trifluoromethylthio-6-chlorophenyl, 2-trifluoromethylthio-6-ethylphenyl, 2-trifluoromethylthio-6-fluorophenyl, 2-methyl-6-thiomethylphenyl, 2-ethyl-6-thiomethylphenyl, 2-fluoro-6-methylthiophenyl, 2-methyl-6-thioethylphenyl, 2-ethyl-6-thioethylphenyl, 2-chloro-6-methylthiophenyl, 2-fluoro-6-ethylthiophenyl, 2-methyl-3,6-difluorophenyl, 2,4,6-trifluorophenyl or 2,6-dichloro-3-methylphenyl; X is an oxygen atom; and $R^1$ is selected from methoxy, ethoxy, isopropoxy, methyl and ethyl and $R^2$ is selected from ethoxy and isopropoxy.

The phosphosulfonate herbicides of formula (I) may be prepared using methods taught by U.S. Pat. No. 5,272,128. The dichloroacetamide safeners of formula (II) may be prepared from dichloroacetyl chloride and the appropriate amine, for example N,N-diallylamine, in the presence of a suitable base using methods well known to those skilled in the art such as those taught by U.S. Pat. No. 4,137,070 and EP 0 648 768 A1.

The following examples 1-3 further illustrate this invention using a phosphosulfonate herbicide (PSH) and a dichloroacetamide safener but is not intended to limit it in any way. The herbicidal test procedure employed is substantially similar to those methods taught by U.S. Pat. No. 5,272,128.

EXAMPLE 1

PREEMERGENCE CONTROL OF WEEDS AND SAFENING EFFECT USING THE HERBICIDAL COMPOSITION CONSISTING OF THE HERBICIDE O-ISOPROPYL P-ETHYL[[(2-CHLORO-6-METHYLPHENYL)SULFONYLOXY]METHYL]PHOSPHINATE (PSH 1) AND THE SAFENER DICHLORMID

| TEST | RATE, G/HA | PERCENT INJURY AFTER 28 DAYS | | | |
|---|---|---|---|---|---|
| | | CRN | FOX | BYG | BLK |
| PSH (1) | 300 | 70 | 100 | 100 | 100 |
| PSH (1) + | 300 | | | | |
| Dichlormid | 4800 | 0 | 100 | 100 | 100 |

EXAMPLE 2

PREEMERGENCE CONTROL OF WEEDS AND SAFENING EFFECT USING THE HERBICIDAL COMPOSITION CONSISTING OF THE HERBICIDE O-ISOPROPYL O-METHYL[[(2-METHYL-6-(TRIFLUOROMETHYL)PHENYL)SULFONYLOXY]METHYL]PHOSPHONATE (PSH 2) AND THE SAFENER FURILAZOLE

| TEST | RATE, G/HA | PERCENT INJURY AFTER 21 DAYS | |
|---|---|---|---|
| | | CRN | BYG |
| PSH (2) | 600 | 40 | 100 |
| PSH (2) + | 600 | | |
| Furilazole | 150 | 0 | 100 |

EXAMPLE 3

PREEMERGENCE CONTROL OF WEEDS AND SAFENING EFFECT USING THE HERBICIDAL COMPOSITION CONSISTING OF THE HERBICIDE O-ISOPROPYL O-METHYL[[(2-ETHYL-6-(TRIFLUOROMETHYL)PHENYL) SULFONYLOXY]METHYL]PHOSPHONATE (PSH 3) AND THE SAFENER FURILAZOLE

| TEST | RATE, G/HA | PERCENT INJURY AFTER 21 DAYS | |
|---|---|---|---|
| | | CRN | BYG |
| PSH (3) | 600 | 30 | 100 |
| PSH (3) + | 600 | | |
| Furilazole | 150 | 0 | 100 |

Footnotes for Examples 1–3:
G/HA = grams/Hectare of substance being tested
CRN = corn (Zea mays)
FOX = Green Foxtail (Setaria viridis)
BYG = Barnyardgrass (Echinochloa crus-galli)
BLK = Blackgrass (Alopecurus myosuroides)

The compositions of this invention are active herbicidally on monocot and dicot weeds, in either pre- or postemergence applications, while showing selectivity to the desired crop. In general, lower doses of the composition are required to control monocot weeds as compared to dicot weeds. In particular, several annual grasses, such as Echinochloa crusgalli, Digitaria sanguinalis and Setaria viridis are especially sensitive. These compositions generally show selectivity to several agronomically important crops such as corn, cotton, rice, soybean, sorghum, peanuts and wheat, most particularly corn. The invention is most effective when formulated in an appropriate carrier, such that the dissolved or dispersed composition is readily applied over the plants or soil in a homogeneous manner.

The invention is also effective when used as a part of a mixture of herbicides formulated in the above manner.

The present composition containing the herbicides and the safener may be applied in any amount which will give the required control of the undesired plants. Generally a rate of application of the herbicide compounds in the composition of this invention is from about 10 grams per hectare to about 8 kilograms per hectare and preferably from about 100 grams per hectare to about 4 kilograms per hectare. Most preferably a rate from about 200 grams per hectare to about 2 kilograms per hectare is used. In general, the amount of safener to be employed in the composition of this invention is from about 100 grams per hectare to about 8 kilograms per hectare and preferably from about 200 grams per hectare to about 4 kilograms per hectare.

The compositions of the present invention are useful for both preemergence and postemergence applications. Preemergence compositions may be applied to the soil surface or incorporated into the soil. Postemergence compositions are those which are applied after the plants have emerged and during their growth period. The compositions of the present invention may be applied to the soil surface prior to plant emergence or incorporated into the soil or other growth medium prior to planting. This incorporation can be carried out by any convenient means, including by simply mixing with the soil by applying the composition to the surface of the soil and then disking or dragging into the soil to the desired depth, or by employing a liquid carrier to accomplish the necessary penetration and impregnation. This invention also contemplates the coating of the seed with the safener component of the instant composition prior to planting and subsequent treatment with the herbicidal component of the instant composition.

A composition of the present invention can be applied postemergence to the growth medium or to plants to be treated either by itself, or, as is generally done, as a component in a herbicidal composition containing additional compounds or a formulation which also comprises an agronomically acceptable carrier.

By agronomically acceptable carrier is meant any substance which can be used to dissolve, disperse or diffuse a herbicidal compound in the composition without impairing the effectiveness of the herbicidal compound and which by itself has no detrimental effect on the soil, equipment, crops or agronomic environment. Mixtures of the herbicidal compounds of the present invention may also be used in any of these herbicidal formulations. The herbicidal compositions of the invention can be either solid or liquid formulations or solutions. For example, the compositions can be formulated as wettable powders, solutions, emulsifiable concentrates, dusts, granular formulations, aerosols, water dispersable granular formulations or flowable concentrates as is known to one skilled in the art. In such formulations, the herbicidal compounds of the composition are extended with a liquid or solid carrier and, when desired, suitable surfactants or emulsifiers are incorporated.

It is usually desirable, particularly in postemergence applications, to include adjuvants such as wetting agents, spreading agents, dispersing agents, sticking agents, adhesives and the like, in accordance with agricultural practices. Examples of adjuvants which are commonly used in the art can be found in the John W. McCutcheon, Inc. publication "Detergents and Emulsifiers Annual."

The compositions of this invention can be dissolved in any appropriate solvent. Examples of solvents which are useful in the practice of this invention include water, alcohols, ketones, aromatic hydrocarbons, halogenated hydrocarbons, dimethylformamide, dioxane, dimethyl sulfoxide and the like. Mixtures of these solvents can also be used. The concentration of compound in the solution can vary from about 2% to about 98%.

The compositions of the present invention can also be mixed with fertilizers or fertilizing materials before their application. In one type of solid fertilizing composition in which the herbicidal compounds and safener in the compositions of the present invention may be used, particles of a fertilizer or fertilizing ingredients, such as ammonium sulfate, ammonium nitrate or ammonium phosphate can be coated with the instant composition. The solid compositions of this invention and solid fertilizing material may also be admixed in blending or mixing equipment, or they can be incorporated with fertilizers in granular formulations. Any relative proportion of herbicidal composition and fertilizer can be used which is suitable for the crops and weeds to be treated.

The compositions of the present invention may be applied as herbicidal sprays by methods commonly employed, such as conventional high-gallonage hydraulic sprays, low gallonage sprays, air blast spray, aerial sprays and dusts. For some applications, two or more of the herbicidal compounds of the instant invention may be combined in the composition, thereby providing additional advantages and effectiveness. When mixtures of the herbicidal compounds of the invention are used, the relative proportion of each compound used will depend on the relative efficacy of the compounds in the mixture with respect to the plants to be treated.

For some applications, one or more other herbicides may be added to the compositions of the present invention, thereby providing additional advantages and effectiveness. When mixtures of herbicides are employed, the relative proportions which are used will depend upon the relative efficacy of compounds in the mixture with respect to the plants to be treated. Examples of other herbicides which can be combined with those of the present invention include:

Carboxylic Acids and Derivatives 2,3,6-trichlorobenzoic acid and its salts;
2,3,5,6-tetrachlorobenzoic acid and its salts;
2-methoxy-3,5,6-trichlorobenzoic acid and its salts;
2-methoxy-3,6-dichlorobenzoic acid and its salts;
2-methyl-3,6-dichlorobenzoic acid and its salts;
2,3-dichloro-6-methylbenzoic acid and its salts;
2,4-dichlorophenoxyacetic acid and its salts and esters;
2,4,5-trichlorophenoxyacetic acid and its salts and esters;
2-methyl-4-chlorophenoxyacetic acid and its salts and esters;
2-(2,4,5-trichlorophenoxy)propionic acid and its salts and esters;
4-(2,4-dichlorophenoxy)butyric acid and its salts and esters;
4-(2-methyl-4-chlorophenoxy)butyric acid and its salts and esters;
2,3,6-trichlorophenylacetic acid and its salts;
3,6-endoxohexahydrophthalic acid and its salts;
dimethyl 2,3,5,6-tetrachloroterephthalate;
trichloroacetic acid and its salts;
2,2-dichloropropionic acid and its salts;
2,3-dichloroisobutyric acid and its salts;
isopropylammonium 2-(4-isopropyl-5-methyl-5-oxo-2-imidazolin-2-yl)nicotinate;
2-[4,5-dihydro-4-methyl-4-(1-methylethyl)-5-oxo-1H-imidazol-2-yl]-3-quinolinecarboxylic acid;
m-toluic acid, 6-(4-isopropyl-4-methyl-5-oxo-2-imidazolin-2-yl)-, methyl ester and
p-toluic acid, 6-(4-isopropyl-4-methyl-5-oxo-2-imidazolin-2-yl)-, methyl ester;
N-(phosphomethyl)glycine isopropylammonium salt;
[3,5,6-trichloro-(2-pyridinyl)oxy]acetic acid;
3,7-dichloro-8-quinolinecarboxylic acid;
ammonium DL-homoalanin-4-yl(methyl)phosphinate.

Carbamic Acid Derivatives ethyl N,N-di(n-propyl)thiolcarbamate;
n-propyl N,N-di(n-propyl)thiolcarbamate;
ethyl N-ethyl-N-(n-butyl)thiolcarbamate;
n-propyl N-ethyl-N-(n-butyl)thiolcarbamate;
2-chloroallyl N,N-diethyldithiocarbamate;
isopropyl N-phenylcarbamate; isopropyl N-(m-chlorophenyl)carbamate;
4-chloro-2-butynyl-N-(m-chlorophenyl)carbamate;
methyl N-(3,4-dichlorophenyl)carbamate;
dinitro-o-(sec-butyl)phenol and its salts;
pentachlorophenol and its salts;
S-(4-chlorobenzyl)-N,N-diethylthiolcarbamate.

Substituted Ureas 2-chloro-N-[(4-methoxy-6-methyl-1,3,5-triazin-2-yl) aminocarbonyl]benzenesulfonamide;
3-(3,4-dichlorophenyl)-1,1-dimethylurea;
3-phenyl-1,1-dimethylurea;
3-(3,4-dichlorophenyl)-3-methoxy-1,1-dimethylurea;
3-(4-chlorophenyl)-3-methoxy-1,1-dimethylurea;
3-(3,4-dichlorophenyl)-1-n-butyl-1-methylurea;
3-(3,4-dichlorophenyl)-1-methoxy-1-methylurea;
3-(4-chlorophenyl)-1-methoxy-1-methylurea;
3-(3,4-dichlorophenyl)-1,1,3-trimethylurea;
3-(3,4-dichlorophenyl)diethylurea;
dichloral urea;
methyl 2-[[[[(4,6-dimethyl-2-pyrimidinyl)amino]carbonyl] amino]sulfonyl]benzoate;
N-((6-methoxy-4-methyl-1,3,5-triazin-2-yl) aminocarbonyl)-2-(2-chloroethoxy)benzenesulfonamide;
2-[[[(4-chloro-6-methoxypyrimidine-2-yl)aminocarbonyl] amino]sulfonyl]benzoic acid, ethyl ester;
methyl 2-[[[[(4-methoxy-6-methyl-1,3,5-triazin-2-yl) amino]carbonyl]amino]sulfonyl]benzoate;
methyl 3-[[(4-methoxy-6-methyl-1,3,5-triazin-2-yl) aminocarbonyl]aminosulfonyl]-2-thiophenecarboxylate;
methyl 2-[[[[(4,6-dimethoxypyrimidin-2-yl)amino] carbonyl]amino]sulfonyl]methyl]benzoate;
methyl 2-[[[[(4-methoxy-6-methyl-1,3,5-triazin-2-yl) methylamino]carbonyl]amino]sulfonyl]benzoate.

Substituted Triazines 2-chloro-4,6-bis(ethylamino)-s-triazine;
2-chloro-4-ethylamino-6-isopropylamino-s-triazine;
2-chloro-4,6-bis(methoxy-n-propylamino)-s-triazine;
2-methoxy-4,6-bis(isopropylamino)-s-triazine;
2-chloro-4-ethylamino-6-(3-methoxy-n-propylamino)-s-triazine;
2-methylmercapto-4,6-bis(isopropylamino)-s-triazine;
2-methylmercapto-4,6-bis(ethylamino)-2-triazine;
2-methylmercapto-4-ethylamino-6-isopropylamino-s-triazine;
2-chloro-4,6-bis(isopropylamino)-s-triazine;
2-methoxy-4-ethylamino-6-isopropylamino-s-triazine;
2-methylmercapto-4-(2-methoxyethylamino)-6-isopropylamino-s-triazine;
4-amino-6-(tert-butyl)-3-(methylthio)-1,2,4-triazine-5(4H)-one.

Diphenyl Ether Derivatives 2,4-dichloro-4'-nitrodiphenyl ether;
2,4,6-trichloro-4'-nitrodiphenyl ether;
2,4-dichloro-6-fluoro-4'-nitrodiphenyl ether;
3-methyl-4'-nitrodiphenyl ether;
3,5-dimethyl-5'-nitrodiphenyl ether;
2,4'-dinitro-4-(trifluoromethyl)diphenyl ether;
2,4-dichloro-3'-methoxy-4'-nitrodiphenyl ether;
sodium 5-(2-chloro-4-(trifluoromethyl)phenoxy)-2-nitrobenzoate;
2-chloro-1-(3-ethoxy-4-nitrophenoxy)-4-(trifluoromethyl) benzene;
1-(carboethoxy)ethyl 5-[2-chloro-4-(trifluoromethyl)-phenoxyl]-2-nitrobenzoate;
5-[2-chloro-4-(trifluoromethyl)phenoxyl]-N-(methylsulphonyl)-2-nitrobenzamide.

Anilides 2-chloro-N-(2-ethyl-6-methylphenyl)-N-(2-methoxy-1-methylethyl)acetamide;
2-chloro-2',6'-diethyl-N-(2-propyloxyethyl)acetanilide;
N-(3,4-dichlorophenyl)propionamide;
N-(3,4-dichlorophenyl)methacrylamide;
N-(3-chloro-4-methylphenyl)-2-methylpentanamide;
N-(3,4-dichlorophenyl)trimethylacetamide;
N-(3,4-dichlorophenyl)-α,α-dimethylvaleramide;
N-isopropyl-N-phenylchloroacetamide;
N-n-butoxymethyl-N-(2,6-diethylphenyl)chloroacetamide;

N-methoxymethyl-N-(2,6-diethylphenyl)chloroacetamide.

Oxyphenoxy Herbicides 2-(4-(2,4-dichlorophenoxy)phenoxy)methyl propionate;
methyl 2-(4-(3-chloro-5-(trifluoromethyl)-2-pyridinyloxy) phenoxy)propanoate;
butyl (R)-2-[4-[5-(trifluoromethyl)-2-pyridinyloxy] phenoxy]propionate;
ethyl 2-[4-[(6-chloro-2-benzoxazolyl)oxy]phenoxy] propanoate;
butyl 2-[4-[[5-(trifluoromethyl)-2-pyridinyl]oxy]phenoxy] propionate;
2-[4-[(6-chloro-2-quinoxalinyl)oxy]phenoxy]propionic acid, ethyl ester.

Uracils 5-bromo-3-sec-butyl-6-methyluracil;
5-bromo-3-cyclohexyl-1,6-dimethyluracil;
3-cyclohexyl-5,6-trimethyleneuracil;
5-bromo-3-isopropyl-6-methyluracil;
3-tert-butyl-5-chloro-6-methyluracil.

Nitriles 2,6-dichlorobenzonitrile; diphenylacetonitrile;
3,5-dibromo-4-hydroxybenzonitrile;
3,5-diiodo-4-hydroxybenzonitrile.

Other Organic Herbicides 2-chloro-N,N-diallylacetamide;
N-(1,1-dimethyl-2-propynyl)-3,5-dichlorobenzamide;
maleic hydrazide;
3-amino-1,2,4-triazole;
monosodium methanearsonate;
disodium methanearsonate;
N,N-dimethyl-α,α-diphenylacetamide;
N-N-di(n-propyl)-2,6-dinitro-4-(trifluoromethyl)aniline;
N,N-di(n-propyl)-2,6-dinitro-4-methylaniline;
N,N-di(n-propyl)-2,6-dinitro-4-methylsulfonylaniline;
O-(2,4-dichlorophenyl)-O-methyl isopropylphosphoramidothioate;
4-amino-3,5,6-trichloropicolinic acid;
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;
6,7-dihydrodipyridol[1,2-a:2',1'-c]pyrazidiium salts;
1,1'-dimethyl-4,4'-bipyridinium salts;
3,4,5,6-tetrahydro-3,5-dimethyl-2-thio-2H-1,3,5-thiadiazine;
2-[1-(ethoxyimino)butyl]-5-[s-(ethylthio)propyl]-3-hydroxy-2-cyclohexen-1-one;
2-(2-chlorophenyl) methyl-4,4-dimethyl-3-isoxazolidinone;
N-(1-ethylpropyl)-3,4-dimethyl-2,6-dinitrobenzamide;
4-chloro-5-(methylamino)-2-(α,α,α-trifluoro-m-toluyl)-3-(2H)-pyridazinone;
2-(3,5-dichlorophenyl)-2-(2,2,2-trichloromethyl)oxirane;
N,N-di(n-propyl)-2,6-dinitro-4-methylaniline;
N,N-di(n-propyl)-2,6-dinitro-4-methylsulfonylaniline;
O-(2,4-dichlorophenyl)-O-methyl isopropylphosphoramidothioate;
4-amino-3,5,6-trichloropicolinic acid;
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;
6,7-di-hydrodipyridol[1,2-a:2',1'-c]pyrazidiium salts;
1,1'-dimethyl-4,4'-bipyridinium salts;
3,4,5,6-tetrahydro-3,5-dimethyl-2-thio-2H-1,3,5-thiadiazine;
2-[1-(ethoxyimino)butyl]-5-[s-(ethylthio)propyl]-3-hydroxy-2-cyclohexen-1-one;
2-(2-chlorophenyl)methyl-4,4-dimethyl-3-isoxazolidinone;
N-(1-ethylpropyl)-3,4-dimethyl-2,6-dinitrobenzamide;
4-chloro-5-(methylamino)-2-(α,α,α-trifluoro-m-toluyl)-3-(2H)-pyridazinone;
2-(3,5-dichlorophenyl)-2-(2,2,2-trichloromethyl)oxirane.

It is to be understood that changes and variations may be made without departing from the spirit and scope of the invention as defined by the appended claims.

We claim:

1. A herbicidal composition of this invention which comprises
(i) one or more phosphosulfonate herbicides having the general formula

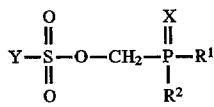

wherein
(1) Y is phenyl; naphthyl; benzyl; ($C_5$–$C_8$)cycloalkyl; a 5-membered heteroaromatic ring having 1, 2, 3, or 4 heteroatoms independently selected from the group consisting of nitrogen, oxygen and sulfur atoms provided no more than one heteroatom is oxygen or sulfur; a 6-membered heteroaromatic ring having 1, 2 or 3 nitrogen atoms; a fused 5,6-membered heteroaromatic ring having 1–4 heteroatoms independently selected from the group consisting of nitrogen, oxygen and sulfur atoms provided no more than one heteroatom is oxygen or sulfur; or a fused 6,6-membered heteroaromatic ring having 1–4 heteroatoms independently selected from the group consisting of nitrogen, oxygen and sulfur atoms provided no more than one heteroatom is oxygen or sulfur;
wherein each of said Y may be substituted with up to three substituents each independently selected from the group consisting of halo, cyano, nitro, alkoxy, haloalkoxy, alkyl, haloalkyl, phenyl, alkylcarbonyloxy, dialkylcarbamoyl, alkylthio, haloalkylthio, arylthio, aryloxy, formyl, alkylcarbonyl, arylcarbonyl, dialkylamino, methoxymethyl, methylmethylthio and alkoxycarbonyl, provided
(a) there is at most one of said substituents on said Y when Y is a thiadiazolyl ring or a tetrazolyl ring,
(b) there is at most two of said substituents when Y is a triazolyl ring, a thiazolyl ring, or an isothiazolyl ring, and
(c) when Y is phenyl, naphthyl or benzyl, there can be one to five of said previously described substituents;
(2) X is an oxygen or a sulfur atom; and
(3) $R^1$ and $R^2$ are each independently selected from the group consisting of alkyl, alkoxy, alkylthio, alkenyloxy, alkynyloxy, haloalkoxy, cyanoalkoxy, alkoxyalkoxy, cycloalkyloxy, cycloalkylalkoxy, alkylideneiminooxy, chloro and amino with one or two substituents selected from the group consisting of alkyl, alkenyl and phenyl; provided that there is no more than one phenyl group on the amino group, and provided that $R^1$ may be selected additionally from phenyl or phenoxy; and provided that $R^1$ and $R^2$ both can be alkoxy, taken together with the phosphorus atom to form a 6-membered oxygen-containing ring, except that when $R^1$ and $R^2$ are both alkoxy, Y is not phenyl, 4-methylphenyl, 4-chlorophenyl, 4-bromophenyl or 3-nitrophenyl;

(ii) a dichloroacetamide safener having the general formula

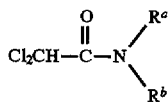

wherein $R^a$ and $R^b$ are each independently alkyl, alkenyl, alkyl or alkenyl substituted with halo, or $R^a$ and $R^b$ together with the nitrogen atom to which they are attached form a 5- or 6-membered substituted heterocyclic ring selected from the group consisting of

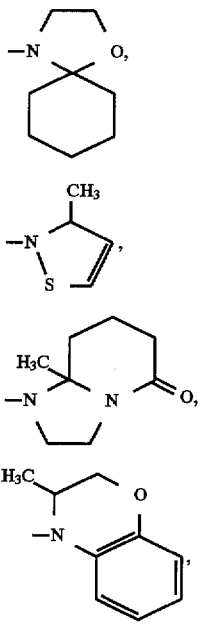

and

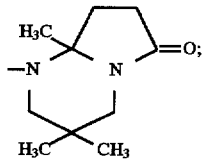

and an agronomically acceptable carrier.

2. The composition of claim 1 wherein each Y may be substituted with up to three substituents each independently selected from the group consisting of halo, cyano, nitro, $(C_1-C_6)$alkoxy, halo$(C_1-C_4)$alkoxy, $(C_1-C_6)$alkyl, halo$(C_1-C_4)$alkyl, phenyl, $(C_1-C_4)$alkylcarbonyloxy, di$(C_1-C_4)$alkylcarbamoyl, $(C_1-C_6)$alkylthio, halo$(C_1-C_4)$alkylthio, arylthio, aryloxy, formyl, $(C_1-C_4)$alkylcarbonyl, arylcarbonyl, di$(C_1-C_4)$alkylamino, methoxymethyl, methylmethylthio and $(C_1-C_4)$alkoxycarbonyl;

$R^1$ and $R^2$ are each independently selected from the group consisting of $(C_1-C_6)$alkyl, $(C_1-C_6)$alkoxy, halo$(C_2-C_4)$alkoxy, $(C_1-C_4)$alkylthio, $(C_3-C_4)$alkenyloxy, $(C_3-C_4)$alkynyloxy, $(C_1-C_4)$alkoxy$(C_1-C_4)$alkoxy, $(C_4-C_8)$cycloalkyloxy, $(C_3-C_6)$cycloalkyl$(C_1-C_3)$ alkoxy, cyano$(C_1-C_4)$alkoxy, $(C_2-C_4)$ alkylideneiminooxy, chloro, and amino substituted with one or two substituents selected from the group consisting of $(C_1-C_4)$alkyl, $(C_2-C_4)$alkenyl and phenyl provided there is not more than one phenyl group on the amino group, additionally, $R^1$ may be phenyl or phenoxy; or $R^1$ and $R^2$ are both alkoxy, taken together with the phosphorous atom to form a 6-membered oxygen-containing ring; and $R^a$ and $R^b$ are each independently $(C_2-C_4)$alkyl, $(C_3-C_4)$ alkenyl, $(C_2-C_4)$alkyl or $(C_3-C_4)$alkenyl substituted with halo.

3. The composition of claim 2 wherein

Y is phenyl having up to three substituents, one of which is at the ortho position, independently selected from the group consisting of halo, cyano, nitro, $(C_1-C_6)$alkoxy, halo$(C_1-C_4)$alkoxy, $(C_1-C_6)$alkyl, halo$(C_1-C_4)$alkyl, phenyl, $(C_1-C_4)$alkylcarbonyloxy, di$(C_1-C_4)$ alkylcarbamoyl, $(C_1-C_6)$alkylthio, halo$(C_1-C_4)$ alkylthio, arylthio, aryloxy, formyl, $(C_1-C_4)$ alkylcarbonyl, arylcarbonyl, di$(C_1-C_4)$alkylamino and $(C_1-C_4)$alkoxycarbonyl;

X is an oxygen atom;

$R^1$ and $R^2$ are each independently selected from the group consisting of $(C_1-C_2)$alkyl and $(C_1-C_4)$alkoxy; provided $R^1$ and $R^2$ are not both alkyl; and $R^a$ and $R^b$ are each independently ethyl, n-propyl, allyl, or ethyl, n-propyl or allyl substituted with chloro.

4. The composition of claim 3 wherein

Y is phenyl, monosubstituted in its ortho position, said substituent being independently selected from the group consisting of chloro, bromo, ethyl, ethoxy, n-propoxy, pentafluoroethyl, methylthio, ethylthio, trifluoromethylthio and trifluoromethyl;

$R^1$ is methoxy, ethoxy, isopropyloxy, methyl or ethyl;

$R^2$ is ethoxy or isopropyloxy; and $R^a$ and $R^b$ are each independently allyl or 3,3-dichloroallyl.

5. The composition of claim 3 wherein

Y is phenyl substituted in its ortho position, the substituent being independently selected from the group consisting of chloro, bromo, trifluoromethoxy, trifluoromethylthio, methylthio, ethylthio and trifluoromethyl; and has a second substituent in its second ortho position selected from the group consisting of chloro, bromo, methyl, ethyl, isopropyl, methoxy, ethoxy, trifluoromethyl, difluoromethyl, difluoromethoxy, trifluoromethylthio, methylthio, ethylthio, pentafluoroethyl, fluoro and trifluoromethoxy;

$R^1$ is methoxy, ethoxy, isopropyloxy, methyl or ethyl;

$R^2$ is ethoxy or isopropyloxy; and $R^a$ and $R^b$ are each independently allyl or 3,3-dichloroallyl.

6. The composition of claim 3 wherein

Y is phenyl substituted with fluoro, chloro or bromo at the two ortho positions and with methyl or ethyl at the meta position;

$R^1$ is methoxy, ethoxy, isopropyloxy, methyl or ethyl;

$R^2$ is ethoxy or isopropyloxy; and $R^a$ and $R^b$ are each independently allyl or 3,3-dichloroallyl.

7. The composition of claim 3 wherein Y is 2-chlorophenyl, 2-bromophenyl, 2,5-dichlorophenyl, 2,6- dichlorophenyl, 2-trifluoromethylphenyl, 2-chloro-6-isopropylphenyl, 2-chloro-6-methylphenyl, 2-methyl-6-trifluoromethylphenyl, 2-methoxy-6-trifluoromethylphenyl, 2-trifluoromethoxyphenyl, 2-methylthiophenyl, 2-ethylthiophenyl, 2-trifluoromethylthiophenyl, 2-trifluoromethyl-6-fluorophenyl, 2-trifluoromethyl-6-ethylphenyl, 2-trifluoromethyl-4-fluorophenyl, 2-trifluoromethyl-6-ethoxyphenyl, 2,5-difluorophenyl, 2-trifluoromethoxy-6-fluorophenyl, 2-trifluoromethyl-6-methylthiophenyl, 2-trifluoromethyl-6-ethylthiophenyl, 2-trifluoromethylthio-4-fluorophenyl, 2-trifluoromethylthio-6-methylphenyl, 2-trifluoromethylthio-6-chlorophenyl, 2-trifluoromethylthio-6-ethylphenyl, 2-trifluoromethylthio-6-fluorophenyl, 2-methyl-6-methylthiophenyl, 2-ethyl-6-methylthiophenyl, 2-fluoro-6-methylthiophenyl, 2-methyl-6-ethylthiophenyl, 2-ethyl-6-ethylthiophenyl, 2-chloro-6-methylthiophenyl, 2-fluoro-6-ethylthiophenyl, 2-methyl-3,6-difluorophenyl, 2,4,6-trifluorophenyl, 2-trifluoromethoxy-6-ethylphenyl, 2-pentafluoroethylphenyl, 2-fluoro-6-methylthiophenyl, 2-methyl-6-ethylthiophenyl, 2-chloro-6-ethylthiophenyl, 2-fluoro-6-ethylthiophenyl, 2-fluoro-6-ethylphenyl, 2-ethyl-3,6-difluorophenyl, or 2,6-dichloro-3-methylphenyl;

$R^1$ is methoxy, ethoxy, isopropyloxy, methyl or ethyl;

$R^2$ is ethoxy or isopropyloxy; and $R^a$ and $R^b$ are each independently allyl or 3,3-dichloroallyl.

8. The composition of claim 7 which consists of one or more of the herbicidal compounds selected from the group consisting of O-isopropyl P-ethyl[[(2-chloro-6-methylphenyl)sulfonyloxy]methyl]phosphinate;

O-isopropyl P-methyl[[(2-chloro-6-methylphenyl)sulfonyloxy]methyl]phosphinate;

O,O-diisopropyl[[(2-chloro-6-methylphenyl)sulfonyloxy]methyl]phosphonate;

O-isopropyl O-ethyl[[(2-chloro-6-methylphenyl)sulfonyloxy]methyl]phosphonate;

O-isopropyl O-methyl[[(2-chloro-6-methylphenyl)sulfonyloxy]methyl]phosphonate;

O-ethyl P-ethyl[[(2-chloro-6-methylphenyl)sulfonyloxy]methyl]phosphinate;

O-ethyl P-methyl[[(2-chloro-6-methylphenyl)sulfonyloxy]methyl]phosphinate;

O-diethyl[[(2-chloro-6-methylphenyl)sulfonyloxy]methyl]phosphonate;

O-ethyl O-methyl[[(2-chloro-6-methylphenyl)sulfonyloxy]methyl]phosphonate;

O-isopropyl P-ethyl[[(2-chloro-6-isopropylphenyl)sulfonyloxy]methyl]phosphinate;

O-isopropyl P-methyl[[(2-chloro-6-isopropylphenyl)sulfonyloxy]methyl]phosphinate;

O-isopropyl O-ethyl[[(2-chloro-6-isopropylphenyl)sulfonyloxy]methyl]phosphonate;

O-isopropyl O-methyl[[(2-chloro-6-isopropylphenyl)sulfonyloxy]methyl]phosphonate;

O,O-diethyl[[(2-chloro-6-isopropylphenyl)sulfonyloxy]methyl]phosphonate;

O,O-diisopropyl[[(2-chloro-6-isopropylphenyl)sulfonyloxy]methyl]phosphonate;

O-ethyl P-methyl-[[(2-chloro-6-isopropylphenyl)sulfonyloxy]methyl]phosphinate;

O-isopropyl P-ethyl[[(2-chlorophenyl)sulfonyloxy]methyl]phosphinate;

O-isopropyl P-methyl[[(2-chlorophenyl)sulfonyloxy]methyl]phosphinate;

O-isopropyl O-ethyl[[(2-chlorophenyl)sulfonyloxy]methyl]phosphonate;

O-isopropyl O-methyl[[(2-chlorophenyl)sulfonyloxy]methyl]phosphonate:

O,O-diethyl[[(2-chlorophenyl)sulfonyloxy]methyl]phosphonate;

O,O-diisopropyl[[(2-chlorophenyl)sulfonyloxy]methyl]phosphonate;

O-isopropyl P-ethyl[[(2-(trifluoromethyl)phenyl)sulfonyloxy]methyl]phosphinate;

O-isopropyl P-methyl[[(2-(trifluoromethyl)phenyl)sulfonyloxy]methyl]phosphinate;

O-isopropyl O-ethyl[[(2-(trifluoromethyl)phenyl)sulfonyloxy]methyl]phosphonate;

O-isopropyl O-methyl[[(2-(trifluoromethyl)phenyl)sulfonyloxy]methyl]phosphonate;

O,O-diethyl[[(2-(trifluoromethyl)phenyl)sulfonyloxy]methyl]phosphonate;

O,O-diisopropyl[[(2-(trifluoromethyl)phenyl)sulfonyloxy]methyl]phosphonate;

O-isopropyl P-ethyl[[(2-(trifluoromethyl)-6-methylphenyl)sulfonyloxy]methyl]-phosphinate;

O-isopropyl P-methyl[[(2-(trifluoromethyl)-6-methylphenyl)sulfonyloxy]methyl]phosphinate;

O-isopropyl O-ethyl[[(2-(trifluoromethyl)-6-methylphenyl)sulfonyloxy]methyl]-phosphonate;

O-isopropyl O-methyl[[(2-(trifluoromethyl)-6-methylphenyl)sulfonyloxy]-methyl]phosphonate;

O-isopropyl P-ethyl[[(2-(trifluoromethyl)-6-methoxyphenyl)sulfonyloxy]methyl]-phosphinate;

O,O-diisopropyl[[(2-(trifluoromethyl)-6-methoxyphenyl)sulfonyloxy]methyl]-phosphonate;

O-isopropyl O-methyl[[(2-(trifluoromethyl)-6-ethylphenyl)sulfonyloxy]methyl]-phosphonate;

O-isopropyl P-methyl[[(2-(trifluoromethyl)-6-methoxyphenyl)sulfonyloxy]-methyl]phosphinate;

O-isopropyl O-ethyl[[(2-(trifluoromethyl)-6-methoxyphenyl)sulfonyloxy]methyl]phosphonate;

O-isopropyl O-methyl[[(2-(trifluoromethyl)-6-methoxyphenyl)sulfonyloxy]-methyl]phosphonate;

O-isopropyl P-ethyl[[(2,6-dichlorophenyl)sulfonyloxy]methyl]phosphinate;

O-isopropyl P-methyl[[(2,6-dichlorophenyl)sulfonyloxy]methyl]phosphinate;

O,O-diisopropyl[[(2,6-dichlorophenyl)sulfonyloxy]methyl]phosphonate;

O-isopropyl O-ethyl[[(2,6-dichlorophenyl)sulfonyloxy]methyl]phosphonate;

O-isopropyl O-methyl[[(2,6-dichlorophenyl)sulfonyloxy]methyl]phosphonate;

O,O-diethyl[[(2,6-dichlorophenyl)sulfonyloxy]methyl]phosphonate;

O,O-diethyl[[(2,5-dichlorophenyl)sulfonyloxy]methyl]phosphonate;

O,O-diisopropyl[[(2,5-dichlorophenyl)sulfonyloxy]methyl]phosphonate;

O-isopropyl P-ethyl[[(2,5-dichlorophenyl)sulfonyloxy]methyl]phosphinate;

O-isopropyl P-methyl[[(2,5-dichlorophenyl)sulfonyloxy]methyl]phosphinate;

O-isopropyl O-ethyl[[(2,5-dichlorophenyl)sulfonyloxy]methyl]phosphonate; and

O-isopropyl O-methyl[[(2,5-dichlorophenyl)sulfonyloxy]methyl]phosphonate;

O,O-diethyl[[(2-(trifluoromethyl)-6-methylphenyl)sulfonyloxy]methyl]phosphonate;

O,O-diisopropyl[[(2-(trifluoromethyl)-6-methylphenyl)sulfonyloxy]methyl]phosphonate;

O,O-diethyl[[(2-(trifluoromethyl)-6-methoxyphenyl)sulfonyloxy]methyl]phosphonate;

O-isopropyl P-methyl[[(2-(trifluoromethyl)-6-ethylphenyl)sulfonyloxy]methyl]phosphinate;

O-isopropyl P-ethyl[[(2-(trifluoromethyl)-6-ethylphenyl)sulfonyloxy]methyl]phosphinate;

O-isopropyl O-ethyl[[(2-(trifluoromethyl)-6-ethylphenyl)sulfonyloxy]methyl]phosphonate;

O,O-diisopropyl[[(2-(trifluoromethyl)-6-ethylphenyl)sulfonyloxy]methyl]phosphonate;

O,O-diethyl[[(2-(trifluoromethyl)-6-ethylphenyl)sulfonyloxy]methyl]phosphonate;

O-isopropyl P-methyl[[(2-(trifluoromethyl)-6-ethoxyphenyl)sulfonyloxy]methyl]phosphinate;

O-isopropyl P-ethyl[[(2-(trifluoromethyl)-6-ethoxyphenyl)sulfonyloxy]methyl]phosphinate;

O-isopropyl O-ethyl[[(2-(trifluoromethyl)-6-ethoxyphenyl)sulfonyloxy]methyl]phosphonate;

O,O-diisopropyl[[(2-(trifluoromethyl)-6-ethoxyphenyl)sulfonyloxy]methyl]phosphonate;

O,O-diethyl[[(2-(trifluoromethyl)-6-ethoxyphenyl)sulfonyloxy]methyl]phosphonate;

O-isopropyl O-methyl[[(2-(trifluoromethyl)-6-ethoxyphenyl)sulfonyloxy]methyl]phosphonate;

O-isopropyl P-methyl[[(2-(trifluoromethyl)-6-fluorophenyl)sulfonyloxy]methyl]phosphinate;

O-isopropyl P-ethyl[[(2-(trifluoromethyl)-6-fluorophenyl)sulfonyloxy]methyl]phosphinate;

O-isopropyl O-ethyl[[(2-(trifluoromethyl)-6-fluorophenyl)sulfonyloxy]methyl]phosphonate;

O,O-diisopropyl[[(2-(trifluoromethyl)-6-fluorophenyl)sulfonyloxy]methyl]phosphonate;

O,O-diethyl[[(2-(trifluoromethyl)-6-fluorophenyl)sulfonyloxy]methyl]phosphonate;

O-isopropyl O-methyl[[(2-(trifluoromethyl)-6-fluorophenyl)sulfonyloxy]methyl]phosphonate;

O-isopropyl P-methyl[[(2-trifluoromethoxyphenyl)sulfonyloxy]methyl]phosphinate;

O-isopropyl P-ethyl[[(2-trifluoromethoxyphenyl)sulfonyloxy]methyl]phosphinate;

O-isopropyl O-ethyl[[(2-trifluoromethoxyphenyl)sulfonyloxy]methyl]phosphonate;

O,O-diisopropyl[[(2-trifluoromethoxyphenyl)sulfonyloxy]methyl]phosphonate;

O,O-diethyl[[(2-trifluoromethoxyphenyl)sulfonyloxy]methyl]phosphonate;

O-isopropyl O-methyl[[(2-trifluoromethoxyphenyl)sulfonyloxy]methyl]phosphonate;

O-isopropyl P-methyl[[(2-(pentafluoroethyl)phenyl)sulfonyloxy]methyl]phosphinate;

O-isopropyl P-ethyl[[(2-(pentafluoroethyl)phenyl)sulfonyloxy]methyl]phosphinate;

O-isopropyl O-ethyl[[(2-(pentafluoroethyl)phenyl)sulfonyloxy]methyl]phosphonate;

O,O-diisopropyl[[(2-(pentafluoroethyl)phenyl)sulfonyloxy]methyl]phosphonate;

O,O-diethyl[[(2-(pentafluoroethyl)phenyl)sulfonyloxy]methyl]phosphonate;

O-isopropyl O-methyl[[(2-(pentafluoroethyl)phenyl)sulfonyloxy]methyl]phosphonate;

O-isopropyl P-methyl[[(2-methylthiophenyl)sulfonyloxy]methyl]phosphinate;

O-isopropyl P-ethyl[[(2-methylthiophenyl)sulfonyloxy]methyl]phosphinate;

O-isopropyl O-ethyl[[(2-methylthiophenyl)sulfonyloxy]methyl]phosphonate;

O,O-diisopropyl[[(2-methylthiophenyl)sulfonyloxy]methyl]phosphonate;

O,O-diethyl[[(2-methylthiophenyl)sulfonyloxy]methyl]phosphonate;

O-isopropyl O-methyl[[(2-methylthiophenyl)sulfonyloxy]methyl]phosphonate;

O-isopropyl P-methyl[[(2-ethylthiophenyl)sulfonyloxy]methyl]phosphinate;

O-isopropyl P-ethyl[[(2-ethylthiophenyl)sulfonyloxy]methyl]phosphinate;

O-isopropyl O-ethyl[[(2-ethylthiophenyl)sulfonyloxy]methyl]phosphonate;

O,O-diisopropyl[[(2-ethylthiophenyl)sulfonyloxy]methyl]phosphonate;

O,O-diethyl[[(2-ethylthiophenyl)sulfonyloxy]methyl]phosphonate;

O-isopropyl O-methyl[[(2-ethylthiophenyl)sulfonyloxy]methyl]phosphonate;

O-isopropyl P-methyl[[(2-trifluoromethylthiophenyl)sulfonyloxy]methyl]phosphinate;

O-isopropyl P-ethyl[[(2-trifluoromethylthiophenyl)sulfonyloxy]methyl]phosphinate;

O-isopropyl O-ethyl[[(2-trifluoromethylthiophenyl)sulfonyloxy]methyl]phosphonate;

O,O-diisopropyl[[(2-trifluoromethylthiophenyl)sulfonyloxy]methyl]phosphonate;

O,O-diethyl[[(2-trifluoromethylthiophenyl)sulfonyloxy]methyl]phosphonate;

O-isopropyl O-methyl[[(2-trifluoromethylthiophenyl)sulfonyloxy]methyl]phosphonate;

O-isopropyl P-methyl[[(2,5-difluorophenyl)sulfonyloxy]methyl]phosphinate;

O-isopropyl P-ethyl[[(2,5-difluorophenyl)sulfonyloxy]methyl]phosphinate;

O-isopropyl O-ethyl[[(2,5-difluorophenyl)sulfonyloxy]methyl]phosphonate;

O,O-diisopropyl[[(2,5-difluorophenyl)sulfonyloxy]methyl]phosphonate;

O,O-diethyl[[(2,5-difluorophenyl)sulfonyloxy]methyl]phosphonate;

O-isopropyl O-methyl[[(2,5-difluorophenyl)sulfonyloxy]methyl]phosphonate;

O-isopropyl P-methyl[[(2-(trifluoromethoxy)-6-fluorophenyl)sulfonyloxy]-methyl]phosphinate;

O-isopropyl P-ethyl[[(2-(trifluoromethoxy)-6-fluorophenyl)sulfonyloxy]methyl]phosphinate;

O-isopropyl O-ethyl[[(2-(trifluoromethoxy)-6-fluorophenyl)sulfonyloxy]methyl]phosphonate;

O,O-diisopropyl[[(2-(trifluoromethoxy)-6-fluorophenyl)sulfonyloxy]methyl]-phosphonate;

O,O-diethyl[[(2-(trifluoromethoxy)-6-fluorophenyl)sulfonyloxy]methyl]phosphonate;

O-isopropyl O-methyl[[(2-(trifluoromethoxy)-6-fluorophenyl)sulfonyloxy]-methyl]phosphonate;

O-isopropyl P-methyl[[(2-(trifluoromethoxy)-6-ethylphenyl)sulfonyloxy]methyl]phosphinate;

O-isopropyl P-ethyl[[(2-(trifluoromethoxy)-6-ethylphenyl)sulfonyloxy]methyl]phosphinate;

O-isopropyl O-ethyl[[(2-(trifluoromethoxy)-6-ethylphenyl)sulfonyloxy]methyl]phosphonate;

O,O-diisopropyl[[(2-(trifluoromethoxy)-6-ethylphenyl)sulfonyloxy]methyl]phosphonate;

O,O-diethyl[[(2-(trifluoromethoxy)-6-ethylphenyl)sulfonyloxy]methyl]phosphonate;

O-isopropyl O-methyl[[(2-(trifluoromethoxy)-6-ethylphenyl)sulfonyloxy]methyl]phosphonate;

O-isopropyl P-methyl[[(2-(trifluoromethyl)-6-methylthiophenyl)sulfonyloxy]-methyl]phosphinate;

O-isopropyl P-ethyl[[(2-(trifluoromethyl)-6-methylthiophenyl)sulfonyloxy]methyl]phosphinate;

O-isopropyl O-ethyl[[(2-(trifluoromethyl)-6-methylthiophenyl)sulfonyloxy]-methyl]phosphonate;

O,O-diisopropyl[[(2-(trifluoromethyl)-6-methylthiophenyl)sulfonyloxy]methyl]phosphonate;

O,O-diethyl[[(2-(trifluoromethyl)-6-methylthiophenyl)sulfonyloxy]methyl]phosphonate;

O-isopropyl O-methyl[[(2-(trifluoromethyl)-6-methylthiophenyl)sulfonyloxy]-methyl]phosphonate;

O-isopropyl P-methyl[[(2-(trifluoromethyl)-6-ethylthiophenyl)sulfonyloxy]-methyl]phosphinate;

O-isopropyl P-ethyl[[(2-(trifluoromethyl)-6-ethylthiophenyl)sulfonyloxy]methyl]phosphinate;

O-isopropyl O-ethyl[[(2-(trifluoromethyl)-6-ethylthiophenyl)sulfonyloxy]-methyl]phosphonate;

O,O-diisopropyl[[(2-(trifluoromethyl)-6-ethylthiophenyl)sulfonyloxy]methyl]phosphonate;

O,O-diethyl[[(2-(trifluoromethyl)-6-ethylthiophenyl)sulfonyloxy]methyl]phosphonate;

O-isopropyl O-methyl[[(2-(trifluoromethyl)-6-ethylthiophenyl)sulfonyloxy]-methyl]phosphonate;

O-isopropyl P-methyl[[(2-(trifluoromethylthio)-4-fluorophenyl)sulfonyloxy]-methyl]phosphinate;

O-isopropyl P-ethyl[[(2-(trifluoromethylthio)-4-fluorophenyl)sulfonyloxy]-methyl]phosphinate;

O-isopropyl O-ethyl[[(2-(trifluoromethylthio)-4-fluorophenyl)sulfonyloxy]-methyl]phosphonate;

O,O-diisopropyl[[(2-(trifluoromethylthio)-4-fluorophenyl)sulfonyloxy]methyl]phosphonate;

O,O-diethyl[[(2-(trifluoromethylthio)-4-fluorophenyl)sulfonyloxy]methy]phosphonate;

O-isopropyl O-methyl[[(2-(trifluoromethylthio)-4-fluorophenyl)sulfonyloxy]-methyl]phosphonate;

O-isopropyl P-methyl[[(2-(trifluoromethylthio)-6-ethylphenyl)sulfonyloxy]-methyl]phosphinate;

O-isopropyl P-ethyl[[(2-(trifluoromethylthio)-6-ethylphenyl)sulfonyloxy]methyl]phosphinate;

O-isopropyl O-ethyl[[(2-(trifluoromethylthio)-6-ethylphenyl)sulfonyloxy]-methyl]phosphonate;

O,O-diisopropyl[[(2-(trifluoromethylthio)-6-ethylphenyl)sulfonyloxy]methyl]phosphonate;

O,O-diethyl[[(2-(trifluoromethylthio)-6-ethylphenyl)sulfonyloxy]methyl]phosphonate;

O-isopropyl O-methyl[[(2-(trifluoromethylthio)-6-ethylphenyl)sulfonyloxy]-methyl]phosphonate;

O-isopropyl P-methyl[[(2-(trifluoromethylthio)-6-methylphenyl)sulfonyloxy]-methyl]phosphinate;

O-isopropyl P-ethyl[[(2-(trifluoromethylthio)-6-methylphenyl)sulfonyloxy]-methyl]phosphinate;

O-isopropyl O-ethyl[[(2-(trifluoromethylthio)-6-methylphenyl)sulfonyloxy]-methyl]phosphonate;

O,O-diisopropyl[[(2-(trifluoromethylthio)-6-methylphenyl)sulfonyloxy]methyl]phosphonate;

O,O-diethyl[[(2-(trifluoromethylthio)-6-methylphenyl)sulfonyloxy]methyl]phosphonate;

O-isopropyl O-methyl[[(2-(trifluoromethylthio)-6-methylphenyl)sulfonyloxy]-methyl]phosphonate;

O-isopropyl P-methyl[[(2-(trifluoromethylthio)-6-chlorophenyl)sulfonyloxy]-methyl]phosphinate;

O-isopropyl P-ethyl[[(2-(trifluoromethylthio)-6-chlorophenyl)sulfonyloxy]-methyl]phosphinate;

O-isopropyl O-ethyl[[(2-(trifluoromethylthio)-6-chlorophenyl)sulfonyloxy]-methyl]phosphonate;

O,O-diisopropyl[[(2-(trifluoromethylthio)-6-chlorophenyl)sulfonyloxy]methyl]phosphonate;

O,O-diethyl[[(2-(trifluoromethylthio)-6-chlorophenyl)sulfonyloxy]methyl]phosphonate;

O-isopropyl O-methyl[[(2-(trifluoromethylthio)-6-chlorophenyl)sulfonyloxy]-methyl]phosphonate;

O-isopropyl P-methyl[[(2-(trifluoromethyl)-4-fluorophenyl)sulfonyloxy]methyl]phosphinate;

O-isopropyl P-ethyl[[(2-(trifluoromethyl)-4-fluorophenyl)sulfonyloxy]methyl]phosphinate;

O-isopropyl O-ethyl[[(2-(trifluoromethyl)-4-fluorophenyl)sulfonyloxy]methyl]phosphonate;

O,O-diisopropyl[[(2-(trifluoromethyl)-4-fluorophenyl)sulfonyloxy]methyl]phosphonate;

O,O-diethyl[[(2-(trifluoromethyl)-4-fluorophenyl)sulfonyloxy]methy]phosphonate;

O-isopropyl O-methyl[[(2-(trifluoromethyl)-4-fluorophenyl)sulfonyloxy]methyl]phosphonate;

O-isopropyl P-methyl[[(2-(trifluoromethylthio)-6-fluorophenyl)sulfonyloxy]-methyl]phosphinate;

O-isopropyl P-ethyl[[(2-(trifluoromethylthio)-6-fluorophenyl)sulfonyloxy]-methyl]phosphinate;

O-isopropyl O-ethyl[[(2-(trifluoromethylthio)-6-fluorophenyl)sulfonyloxy]-methyl]phosphonate;

O,O-diisopropyl[[(2-(trifluoromethylthio)-6-fluorophenyl)sulfonyloxy]methyl]phosphonate;

O,O-diethyl[[(2-(trifluoromethylthio)-6-fluorophenyl)sulfonyloxy]methyl]phosphonate;

O-isopropyl O-methyl[[(2-(trifluoromethylthio)-6-fluorophenyl)sulfonyloxy]-methyl]phosphonate;

O-isopropyl P-methyl[[(2-methyl-6-methylthiophenyl)sulfonyloxy]methyl]phosphinate;

O-isopropyl P-ethyl[[(2-methyl-6-methylthiophenyl)sulfonyloxy]methyl]phosphinate;

O-isopropyl O-ethyl[[(2-methyl-6-methylthiophenyl)sulfonyloxy]methyl]phosphonate;

O,O-diisopropyl[[(2-methyl-6-methylthiophenyl)sulfonyloxy]methyl]phosphonate;

O,O-diethyl[[(2-methyl-6-methylthiophenyl)sulfonyloxy]methyl]phosphonate;

O-isopropyl O-methyl[[(2-methyl-6-methylthiophenyl)sulfonyloxy]methyl]phosphonate;

O-isopropyl P-methyl[[(2-ethyl-6-methylthiophenyl)sulfonyloxy]methyl]phosphinate;

O-isopropyl P-ethyl[[(2-ethyl-6-methylthiophenyl)sulfonyloxy]methyl]phosphinate;

O-isopropyl O-ethyl[[(2-ethyl-6-methylthiophenyl)sulfonyloxy]methyl]phosphonate;

O,O-diisopropyl[[(2-ethyl-6-methylthiophenyl)sulfonyloxy]methyl]phosphonate;

O,O-diethyl[[(2-ethyl-6-methylthiophenyl)sulfonyloxy]methyl]phosphonate;

O-isopropyl O-methyl[[(2-ethyl-6-methylthiophenyl)sulfonyloxy]methyl]phosphonate;

O-isopropyl P-methyl[[(2-fluoro-6-methylthiophenyl)sulfonyloxy]methyl]phosphinate;

O-isopropyl P-ethyl[[(2-fluoro-6-methylthiophenyl)sulfonyloxy]methyl]phosphinate;

O-isopropyl O-ethyl[[(2-fluoro-6-methylthiophenyl)sulfonyloxy]methyl]phosphonate;

O,O-diisopropyl[[(2-fluoro-6-methylthiophenyl)sulfonyloxy]methyl]phosphonate;

O,O-diethyl[[(2-fluoro-6-methylthiophenyl)sulfonyloxy]methyl]phosphonate;

O-isopropyl O-methyl[[(2-fluoro-6-methylthiophenyl)sulfonyloxy]methyl]phosphonate;

O-isopropyl P-methyl[[(2-methyl-6-ethylthiophenyl)sulfonyloxy]methyl]phosphinate;

O-isopropyl P-ethyl[[(2-methyl-6-ethylthiophenyl)sulfonyloxy]methyl]phosphinate;

O-isopropyl O-ethyl[[(2-methyl-6-ethylthiophenyl)sulfonyloxy]methyl]phosphonate;

O,O-diisopropyl[[(2-methyl-6-ethylthiophenyl)sulfonyloxy]methyl]phosphonate;

O,O-diethyl[[(2-methyl-6-ethylthiophenyl)sulfonyloxy]methyl]phosphonate;

O-isopropyl O-methyl[[(2-methyl-6-ethylthiophenyl)sulfonyloxy]methyl]phosphonate;

O-isopropyl P-methyl[[(2-ethyl-6-ethylthiophenyl)sulfonyloxy]methyl]phosphinate;

O-isopropyl P-ethyl[[(2-ethyl-6-ethylthiophenyl)sulfonyloxy]methyl]phosphinate;

O-isopropyl O-ethyl[[(2-ethyl-6-ethylthiophenyl)sulfonyloxy]methyl]phosphonate;

O,O-diisopropyl[[(2-ethyl-6-ethylthiophenyl)sulfonyloxy]methyl]phosphonate;

O,O-diethyl[[(2-ethyl-6-ethylthiophenyl)sulfonyloxy]methyl]phosphonate;

O-isopropyl O-methyl[[(2-ethyl-6-ethylthiophenyl)sulfonyloxy]methyl]phosphonate;

O-isopropyl P-methyl[[(2-chloro-6-ethylthiophenyl)sulfonyloxy]methyl]phosphinate;

O-isopropyl P-ethyl[[(2-chloro-6-ethylthiophenyl)sulfonyloxy]methyl]phosphinate;

O-isopropyl O-ethyl[[(2-chloro-6-ethylthiophenyl)sulfonyloxy]methyl]phosphonate;

O,O-diisopropyl[[(2-chloro-6-ethylthiophenyl)sulfonyloxy]methyl]phosphonate;

O,O-diethyl[[(2-chloro-6-ethylthiophenyl)sulfonyloxy]methyl]phosphonate;

O-isopropyl O-methyl[[(2-chloro-6-ethylthiophenyl)sulfonyloxy]methyl]phosphonate;

O-isopropyl P-methyl[[(2-fluoro-6-ethylthiophenyl)sulfonyloxy]methyl]phosphinate;

O-isopropyl P-ethyl[[(2-fluoro-6-ethylthiophenyl)sulfonyloxy]methyl]phosphinate;

O-isopropyl O-ethyl[[(2-fluoro-6-ethylthiophenyl)sulfonyloxy]methyl]phosphonate;

O,O-diisopropyl[[(2-fluoro-6-ethylthiophenyl)sulfonyloxy]methyl]phosphonate;

O,O-diethyl[[(2-fluoro-6-ethylthiophenyl)sulfonyloxy]methyl]phosphonate;

O-isopropyl O-methyl[[(2-fluoro-6-ethylthiophenyl)sulfonyloxy]methyl]phosphonate;

O-isopropyl P-methyl[[(2-fluoro-6-ethylphenyl)sulfonyloxy]methyl]phosphinate;

O-isopropyl P-ethyl[[(2-fluoro-6-ethylphenyl)sulfonyloxy]methyl]phosphinate;

O-isopropyl O-ethyl[[(2-fluoro-6-ethylphenyl)sulfonyloxy]methyl]phosphonate;

O,O-diisopropyl[[(2-fluoro-6-ethylphenyl)sulfonyloxy]methyl]phosphonate;

O,O-diethyl[[(2-fluoro-6-ethylphenyl)sulfonyloxy]methyl]phosphonate;

O-isopropyl O-methyl[[(2-fluoro-6-ethylphenyl)sulfonyloxy]methyl]phosphonate;

O-isopropyl P-methyl[[(2-methyl-3,6-difluorophenyl)sulfonyloxy]methyl]phosphinate;

O-isopropyl P-ethyl[[(2-methyl-3,6-difluorophenyl)sulfonyloxy]methyl]phosphinate;

O-isopropyl O-ethyl[[(2-methyl-3,6-difluorophenyl)sulfonyloxy]methyl]phosphonate;

O,O-diisopropyl[[(2-methyl-3,6-difluorophenyl)sulfonyloxy]methyl]phosphonate;

O,O-diethyl[[(2-methyl-3,6-difluorophenyl)sulfonyloxy]methyl]phosphonate;

O-isopropyl O-methyl[[(2-methyl-3,6-difluorophenyl)sulfonyloxy]methyl]phosphonate;

O-isopropyl P-methyl[[(2-ethyl-3,6-difluorophenyl)sulfonyloxy]methyl]phosphinate;

O-isopropyl P-ethyl[[(2-ethyl-3,6-difluorophenyl)sulfonyloxy]methyl]phosphinate;

O-isopropyl O-ethyl[[(2-ethyl-3,6-difluorophenyl)sulfonyloxy]methyl]phosphonate;

O,O-diisopropyl[[(2-ethyl-3,6-difluorophenyl)sulfonyloxy]methyl]phosphonate;

O,O-diethyl[[(2-ethyl-3,6-difluorophenyl)sulfonyloxy]methyl]phosphonate;

O-isopropyl O-ethyl[[(2-methyl-3,6-difluorophenyl)sulfonyloxy]methyl]phosphonate;

O-isopropyl P-methyl[[(2,4,6-trifluorophenyl)sulfonyloxy]methyl]phosphinate;

O-isopropyl P-ethyl[[(2,4,6-trifluorophenyl)sulfonyloxy]methyl]phosphinate;

O-isopropyl O-ethyl[[(2,4,6-trifluorophenyl)sulfonyloxy]methyl]phosphonate;

O,O-diisopropyl[[(2,4,6-trifluorophenyl)sulfonyloxy]methyl]phosphonate;

O,O-diethyl[[(2,4,6-trifluorophenyl)sulfonyloxy]methyl]phosphonate;

O-isopropyl O-methyl[[(2,4,6-trifluorophenyl)sulfonyloxy]methyl]phosphonate; and a safener selected from N,N-diallyldichloroacetamide and N,N-bis(3,3-dichloroallyl)dichloroacetamide.

9. The composition of claim 2 wherein

Y is a 5-membered unsubstituted or substituted heterocyclic substituent selected from the group consisting of thienyl, pyrazolyl, isoxazolyl, triazolyl, tetrazolyl, thiazolyl, isothiazolyl, pyrrolyl, thiadiazolyl, pyrimidinyl, and imidazolyl; and $R^a$ and $R^b$ are each independently ethyl, n-propyl, allyl, or ethyl, n-propyl or allyl substituted with chloro.

10. The composition of claim 9 wherein Y is pyrimidin-2-yl, pyrimidinyl-4-yl or pyrimidin-5-yl and $R^a$ and $R^b$ are each independently allyl or 3,3-dichloroallyl.

11. The composition of claim 2 wherein Y is a fused 5,6-membered heteroaromatic substituent selected from the group consisting of indolyl, imidazolpyridinyl, benzoimidazolyl, benzothienyl, benzothiazolyl, benzothiadiazolyl, benzotriazolyl, benzoxazolyl, and pyrazolopyrimidinyl; and $R^a$ and $R^b$ are each independently ethyl, n-propyl, allyl, or ethyl, n-propyl or allyl substituted with chloro.

12. The composition of claim 9 wherein Y is 5-chloro-1-methyl-3-($C_1$–$C_3$)alkyl-4-pyrazolyl; $R^1$ is isopropoxy; $R^2$ is methyl, ethyl, methoxy, or ethoxy; and $R^a$ and $R^b$ are each independently allyl or 3,3-dichloroallyl.

13. The composition of claim 12 wherein $R^2$ is methyl or ethyl.

14. A method for controlling unwanted plants which comprises applying to the seed, plant or growth medium therefore the composition of claim 1.

15. A method for controlling unwanted plants which comprises applying to the seed, plant or growth medium therefore the composition of claim 2.

\* \* \* \* \*